United States Patent [19]

VandenBerg

[11] Patent Number: Plant 6,947

[45] Date of Patent: Jul. 25, 1989

[54] CHRYSANTHEMUM PLANT NAMED NIMBA

[75] Inventor: Cornelis P. VandenBerg, Salinas, Calif.

[73] Assignee: Yoder Brothers, Inc., Barberton, Ohio

[21] Appl. No.: 218,983

[22] Filed: Jul. 14, 1988

[51] Int. Cl.[4] ..... A01H 5/00

[52] U.S. Cl. ..... Plt./77

[58] Field of Search ..... Plt./77

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Nimba particularly characterized by its small pompon capitulum form; formal decorative capitulum type; white ray floret color; diameter across face of capitulum of up to 4.5 cm at maturity; uniform eight week photoperiodic flowering response to short days; peduncle length ranging from 10 to 18 cm on open, terminal sprays; and medium plant height when grown as a single stem spray cut mum.

3 Drawing Sheets

The present invention comprises a new and distinct cultivar of Chrysanthemum, botanically known as *Dendranthema grandiflora,* and referred to by the cultivar name Nimba.

Nimba, identified as 85879009, was originated from a cross made in a controlled breeding program in Salinas, Calif. in 1985.

The female parent of Nimba was the cultivar Butterball, disclosed in U.S. Plant Pat. No. 4,556. The male parent was the cultivar Elfin, disclosed in U.S. Plant Pat. No. 5,810.

Nimba was discovered and selected as one flowering plant within the progeny of the stated cross by Cornelis P. VandenBerg on Sept. 10, 1985 in a controlled environment in Salinas, Calif.

The first act of asexual reproduction of Nimba was accomplished when vegetative cuttings were taken from the initial selection in November 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Nimba are firmly fixed and are retained through successive generations of asexual reproduction.

Nimba has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Nimba, which, in combination, distinguish this Chrysanthemum as a new and distinct cultivar:

1. Small pompon capitulum form.
2. Formal decorative capitulum type.
3. White ray floret color.
4. Diameter across face of capitulum up to 4.5 cm at maturity.
5. Uniform eight week photoperiodic flowering response to short days.

6. Peduncle length ranging from 10 to 18 cm on open terminal sprays.
7. Medium plant height, requiring two long day weeks prior to short days to attain a flowered plant height of 90 to 100 cm for year-round flowerings.

The accompanying photographic drawings show typical inflorescence and leaf characteristics of Nimba, with the colors being as nearly true as possible with illustrations of this type.

Sheet 1 is a color photograph of Nimba grown as a single stem cut spray mum.

Sheet 2 is a black and white photograph of three views of the inflorescence of Nimba.

Sheet 3 is a black and white photograph showing the upper and under sides of the leaves of Nimba at three stages of development (mature, intermediate and immature).

Of the commercial cultivars known to the inventor, the most similar in comparison to Nimba is the unpatented cultivar Cottonball. Reference is made to Chart A, which compares certain characteristics of Nimba to the same characteristics of Cottonball.

Similar traits are ray floret color and capitulum form and type. The spray formation of Nimba is terminal, while Cottonball generally shows a compound spray formation. Nimba has longer peduncles, a slightly larger capitulum diameter, taller plant height and a shorter flowering response period than Cottonball.

In the following description, color references are made to The Royal Horticultural Society Colour Chart. The color values were determined on plant material grown in Salinas, Calif. on Apr. 22, 1988.

Classification:

*Botanical.*—*Dendranthema grandiflora,* cv Nimba.

*Commercial.*—Small pompon formal decorative cut spray mum.

INFLORESCENCE

A. Capitulum:

*Form.*—Small pompon.

*Type.*—Formal decorative.

*Diameter across face.*—Up to 4.5 cm at maturity.

B. Corolla of ray florets:

*Color (general tonality from a distance of three meters).*—White.

*Color (upper surface).*—155B, with center of capitulum 157A.

*Color (under surface).*—155B.

*Shape.*—Straight. Crossection concave, oblong.

C. Corolla of disc florets:

*Color (mature).*—Closest to 7A.

*Color (immature).*—Closest to 144B.

D. Reproductive organs:

*Androecium.*—Present on disc florets only; few disc florets, visible in the center of the capitulum.

*Gynoecium.*—Present on both ray and disc florets.

PLANT

A. General appearance:

*Height.*—Medium; 90 to 100 cm as a single stem cut mum with 2 long day weeks prior to short days.

B. Foliage:

*Color (upper surface).*—137A.

*Color (under surface).*—137B.

*Shape.*—Lobed and slightly serrated.

CHART A

COMPARISON OF NIMBA AND COTTONBALL

| | Nimba | Cottonball |
|---|---|---|
| Ray floret color | White | White |
| Capitulum form and type | Small<br>Pompon<br>Formal<br>Decorative | Small<br>Pompon<br>Formal<br>Decorative |
| Spray formation | Terminal<br>10 to 18 cm | Compound<br>8 to 15 cm |
| Diameter across face of capitulum | Up to 4.5 cm | Up to 3.5 cm |
| Plant height | Medium | Short |
| Flowering response period | 8 weeks | 9 weeks |

COMPARISONS MADE OF PLANTS GROWN AS SINGLE STEM SPRAY CUT MUMS IN SALINAS, CALIFORNIA

I claim:

1. A new and distinct Chrysanthemum plant named Nimba, as described and illustrated.

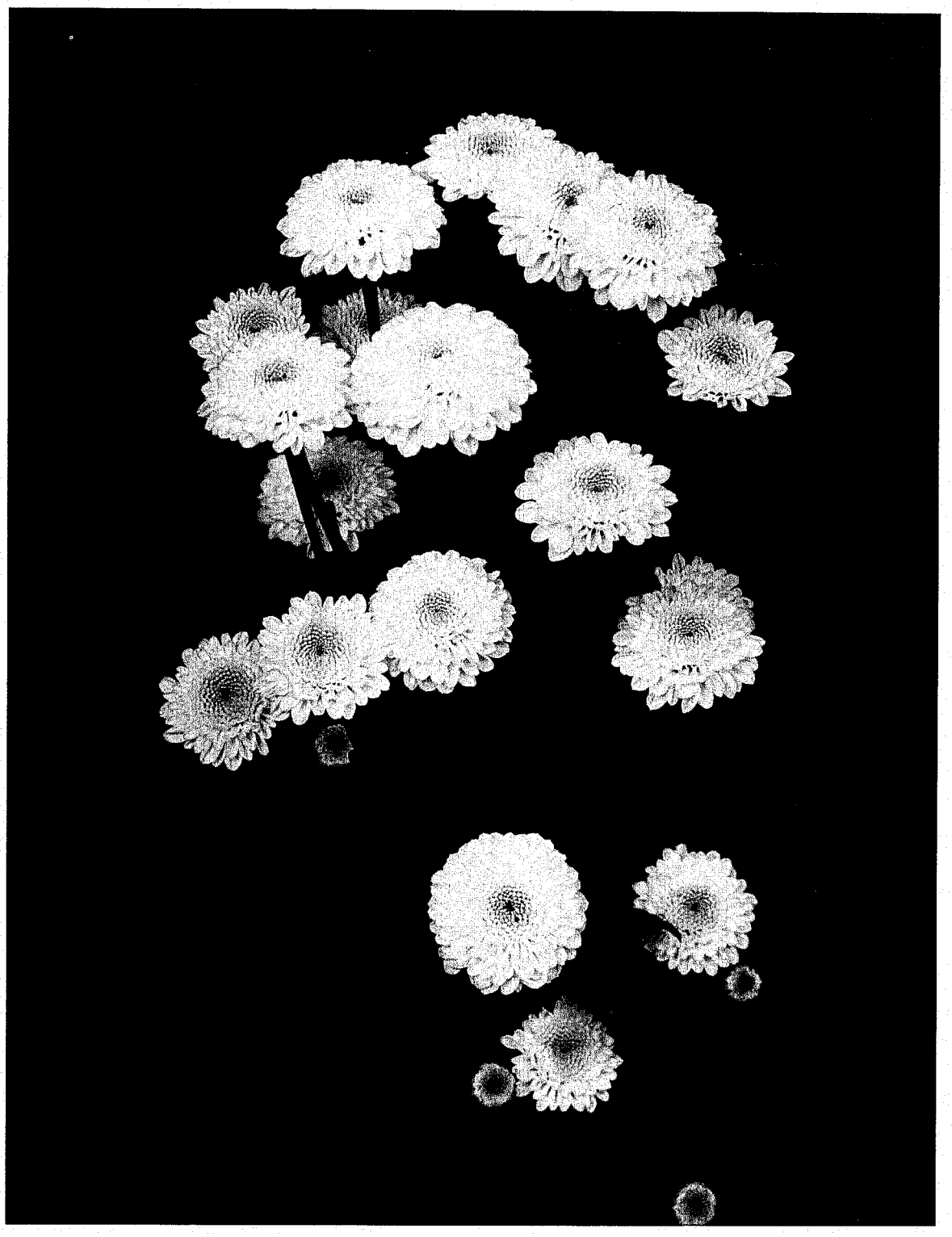

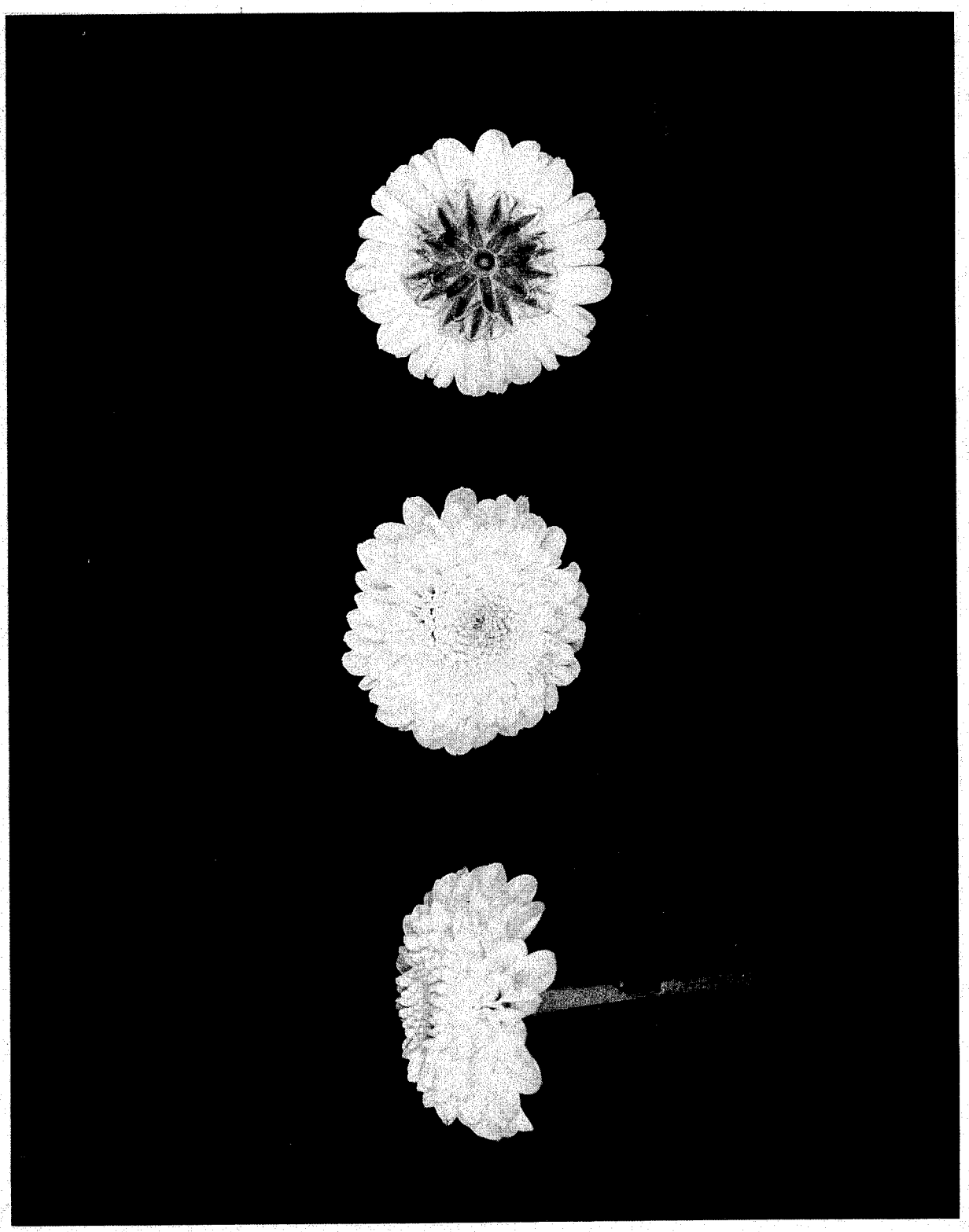

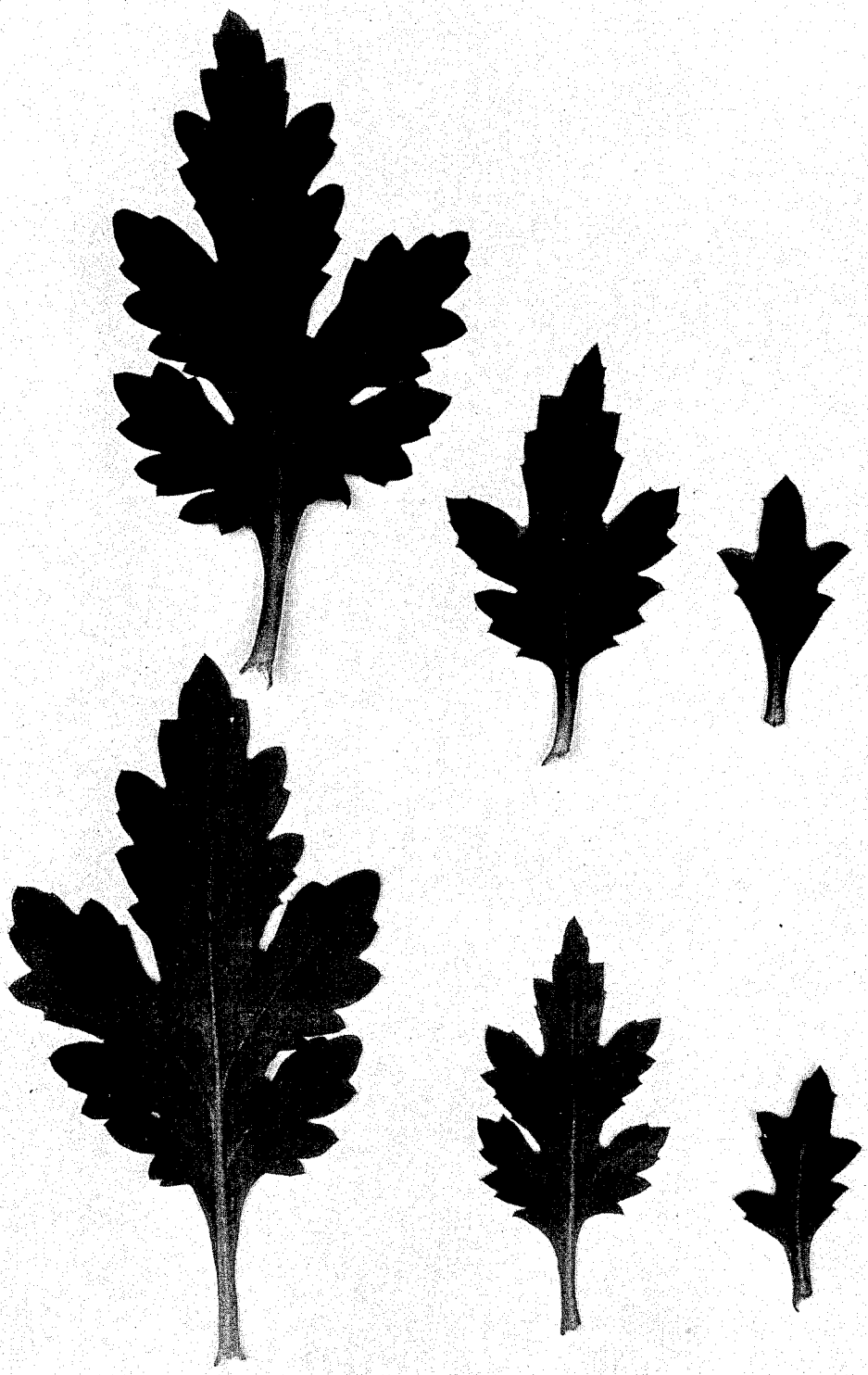

* * * * *